United States Patent [19]

Naito et al.

[11] 4,103,085
[45] Jul. 25, 1978

[54] 7-(SYN-α-ALKOXY-IMINOFURYLACETAMIDO-3-(2-CARBOXY-ALKYL-2,3-DIHYDRO-S-TRIAZOLO[4,3-b]PYRIDAZIN-3-ON-6-YLTHIOMETHYL)-3-CEPHEM-4-CARBOXYLIC ACIDS

[75] Inventors: Takayuki Naito, Kawasaki; Jun Okumura, Yokohama; Seiji Iimura, Tokyo, all of Japan

[73] Assignee: Bristol-Myers Company, New York, N.Y.

[21] Appl. No.: 771,859

[22] Filed: Feb. 24, 1977

[51] Int. Cl.² ............................................. C07D 501/36
[52] U.S. Cl. .................................... 544/27; 544/236; 544/26; 424/246; 260/347.3; 260/347.8
[58] Field of Search ........................ 544/19, 21, 26, 27, 544/30

[56] References Cited

U.S. PATENT DOCUMENTS 4,024,134  8/1977  Gregson et al. ................. 424/246

*Primary Examiner*—Donald G. Daus
*Assistant Examiner*—David E. Wheeler
*Attorney, Agent, or Firm*—Herbert W. Taylor, Jr.

[57] ABSTRACT

Cephalosporins in a series having the formula

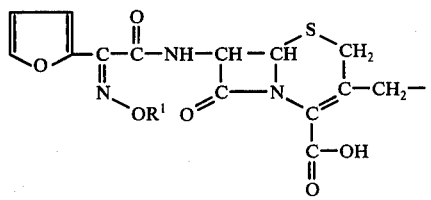

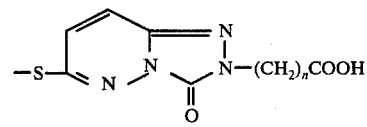

wherein R¹ is alkyl containing 1-4 carbon atoms and *n* is 1 or 2 or a nontoxic pharmaceutically acceptable salt thereof, were synthesized and found to be potent antibacterial agents especially when in the form of the syn isomers essentially free of the corresponding anti isomer.

9 Claims, No Drawings

7-(SYN-α-ALKOXY-IMINOFURYLACETAMIDO-3-(2-CARBOXYALKYL-2,3-DIHYDRO-S-TRIAZOLO[4,3-b]PYRIDAZIN-3-ON-6-YLTHIOMETHYL)-3-CEPHEM-4-CARBOXYLIC ACIDS

BACKGROUND OF THE INVENTION

1. Field of the Invention

The cephalosporins of the present invention in general possess the usual attributes of such compounds and are particularly useful in the treatment of bacterial infections.

2. Description of the Prior Art

U.K. Pat. No. 1,399,086 discloses antibiotic compounds of the general formula

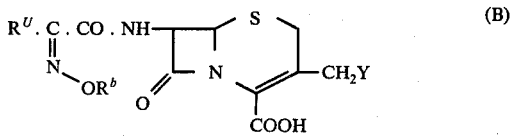

(wherein $R^U$ is phenyl; naphthyl; thienyl; furyl, benzothienyl; benzofuryl; pyridyl or any of these groups substituted by halo (chloro, bromo, iodo or fluoro), hydroxy, lower alkyl, nitro, amino, loweralkylamino, diloweralkylamino, lower alkanoyl, lower alkanoylamino, lower alkoxy, lower alkylthio or carbamoyl; $R^b$ is lower alkyl; cycloalkyl containing 3–7 carbon atoms; carbocyclic or heterocyclic aryl lower alkyl or any of these groups substituted by hydroxy, carboxy, exterified carboxy, amido, cyano, alkanoyl, amino, substituted amino, halogen or lower alkoxy; and Y is selected from acetoxy; a group of formula

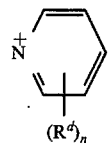

where $R^d$ and $n$ are as defined in claim 19; a group of formula —SW where W is thiadiazolyl, diazolyl, triazolyl, tetrazolyl, thiazolyl, thiatriazolyl, oxazolyl, oxadiazolyl, benzimidazolyl, benzoxazolyl, triazolopyridyl, purinyl, pyridyl or pyrimidyl; an alkylthio group containing 1–4 carbon atoms; a group of formula —O.CO.$R^9$ where $R^9$ is an alkyl or alkenyl group containing 2–4 carbon atoms; the group —O.CO.NH.$(CH_2)_m$D wherein $m$ is an integer of from 1–4 and D is chlorine, bromine, iodine or fluorine; and azido) and non-toxic salts and esters thereof. Methods for the preparation of the starting acids used to form the 7-substituent, including their separation into syn and anti isomers, are also described therein and in U.K. Pat No. 1,404,221.

Presently issued U.S. Pat. Nos. 3,966,717 and 3,971,778 (with many nucleophilic substituents) contain at least part of the disclosure of U.K. Pat. No. 1,399,086 as does U.S. Pat. No. 3,974,153. See also Farmdoc abstracts 17270X and 19177X and 63415X (which also contains thiol substitution).

U.S. Pat. No. 3,974,153 claims compounds of the formula

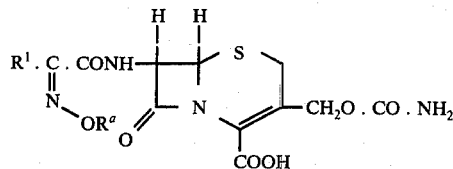

wherein $R^1$ is furyl, thienyl or phenyl; and $R^a$ is $C_{1-4}$ alkyl, $C_{3-7}$ cycloalkyl or phenyl; and a physiologically acceptable salt thereof.

With reference to cephalosporins in which the acetoxy group in the 3-methyl substituent has been displaced by a thiol see U.S. Pat. No. 3,741,965 for a review of the older art. Specific disclosures of 3-substituents having the formula —$CH_2$—S—Het wherein Het is an aromatic, five membered ring containing at least two heterocyclic atoms and also having a substituent on that ring other than alkyl or aralkyl are found, for example, in U.S. Pat. Nos. 3,719,673, 3,757,014, 3,799,923 and 3,910,899. See also U.S. Pat. Nos. 3,516,997 and 3,819,623 and Farmdoc abstract 77919X.

U.S. Pat. Nos. 3,772,286, 3,812,116, 3,867,380, 3,912,728, 3,931,160 and 3,947,413 and U.K. Pat. No. 1,461,948 and Farmdoc (Derwent) abstracts 00145W, 22850W, 82150X, 68777X, 65694X, 02692X and 58433X make reference to 3-heterocyclicthiomethyl cephalosporins containing a number of substituents on the numerous heterocycles included but these references are completely general in nature and except for a few working examples include no physical constants, yields, methods of synthesis or the like and often do not even name the final compound. In most instances no method of preparation of the thiol itself is given or referred to and it often seems probable that they are novel compounds when the substituents are other than simple alkyl or aryl groups.

For examples of publications in the scientific literature see Ryan et al., Antimicrobial Agents and Chemotherapy, 9, 520–525 (1976) and O'Callaghan et al., ibid, 9, 511–519 (1976) and Norby et al., ibid, 9, 506–510 (1976) regarding cefuroxime and Leitner et al., ibid, 10(3), 426–435 (Sept. 1976) regarding BL-S786.

U.S. Pat. No. 3,819,623 discloses the conversion of the 2-mercapto-1,3,4-thiadiazole-5-acetic acid to 7-(1H-tetrazol-1-yl-acetamido)-3-(5-carboxymethyl-1,3,4-thiadiazol-2-ylthiomethyl)-3-cephem-4-carboxylic acid and see also Farmdoc abstract 12921T.

Farmdoc abstract 18830X discloses acids of the formula

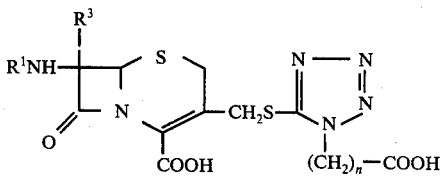

(where $R^1$ = acyl or H; $R^3$ = H or methoxy; $n$ = 1–9) and esters thereof. The compounds of the present invention are not described therein or in the full text of the corresponding patent. See also Farmdoc abstracts 01981X and 58433X and 52086X and 44686X and West Germany 2514322 (Farmdoc 69292W) and West Germany 2518582 (Ex. 6) (Farmdoc 74126W). See U.S. Pat.

No. 3,989,694 and Farmdoc 01981X and Farmdoc 73990X for a similarly substituted triazole.

SUMMARY OF THE INVENTION

One of the problems presently facing the medical profession at this time was described by Arnold L. Smith, M.D. in an article titled Antibiotics and Invasive *Haemophilus influenzae*, N. Engl. J. Med., 294(24), 1329–1331 (June 10, 1976) in which the opening sentence reads as follows: "Recently, the information service of the Center for Disease Control, the Medical Letter and the Americal Academy of Pediatrics have sounded the alert that invasive strains of *Haemophilus influenzae* isolated throughout the United States have been found to be resistant to ampicillin, many of the isolates being associated with treatment failure." His concluding paragraph reads: "The current situation portends a dismal future for the antibiotic treatment of invasive *H. influenzae* disease. An *H. influenzae* resistant to the second-line drug, chloramphenicol, has been described, and, more recently, an untypable *H. influenzae resistant to chloramphenicol and tetracycline was isolated from the throat of a* 4-year-old girl. Thus, both these currently efficacious agents may not be useful in the future."

A solution to this problem is provided by the present invention.

The present invention thus provides compounds having the formula

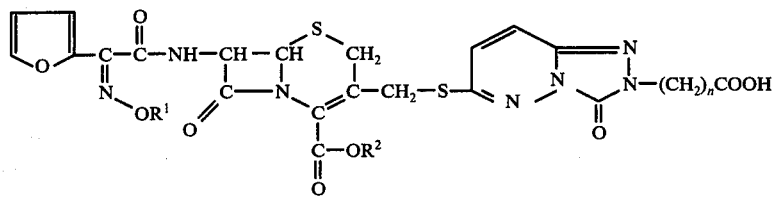

often written herein as

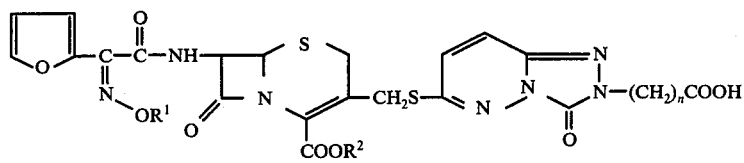

wherein $R^1$ is alkyl containing 1–4 carbon atoms, $n$ is 1 or 2 and $R^2$ is hydrogen or a conventional, pharmaceutically acceptable, easily hydrolyzed ester forming group such as those set forth below and including the group having the formula

wherein when W represents hydrogen, Z represents (lower)alkanoyl, benzoyl, naphthoyl, furoyl, thenoyl, nitrobenzoyl, methylbenzoyl, halobenzoyl, phenylbenzoyl, N-phthalimido, N-succinimido, N-saccharino, N-(lower)alkylcarbamoyl, (lower)alkoxy, (lower)alkylthio, phenoxy, carbalkoxy, carbobenzoxy, carbamoyl, benzyloxy, chlorobenzyloxy, carbophenoxy, carbo-tert.-butoxy or (lower)alkylsulfonyl, and when W represents carbalkoxy, Z represents carbalkoxy and, when W represents phenyl, Z represents benzoyl or cyano or wherein W and Z taken together represent 2-oxocycloalkyl containing 4 to 8 carbon atoms inclusive.

As set forth below in more detail the present invention also provides salts of these acids. The stereochemistry of the bicyclic nucleus is that found in Cephalosporin C.

The compounds of the present invention are syn isomers or else are mixtures of syn and anti isomers containing at least 75% of the syn isomer. Preferably such mixtures of isomers contain at least 90% of the syn isomer and not more than 10% of the anti isomer. Most preferably the compounds are syn isomers essentially free of the corresponding anti isomer.

The preferred embodiments of the present invention are the syn isomers of the compounds of Formula I wherein $R^1$ is methyl or ethyl, $n$ is 1 or 2 and $R^2$ is hydrogen, pivaloyloxymethyl, acetoxymethyl, methoxymethyl, acetonyl, phenacyl, p-nitrobenzyl, $\beta,\beta,\beta$-trichloroethyl, 3-phthalidyl or 5-indanyl.

Reference to the syn (cis) isomeric form refers to the configuration of the group $OR^1$ with respect to the carboxamido group. The present invention also provides the process for the production of the antibacterial agents having the formula

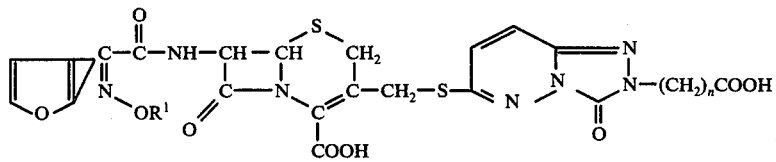

wherein $R^1$ is alkyl containing 1–4 carbon atoms and $n$ is 1 or 2 which comprises reacting a compound of the formula

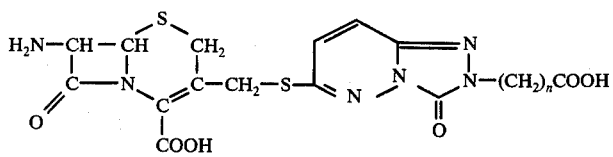

II wherein n is 1 or 2 or a salt or easily hydrolyzed ester or Schiff base as with benzaldehyde or salicylaldehyde thereof (including, but not limited to, those of U.S. Pat. No. 3,284,451 and U.K. Pat. No. 1,229,453 and any of the silyl esters described in U.S. Pat. No. 3,249,622 for use with 7-aminopenicillanic acid and used in Great Britain Pat. No. 1,073,530 and particularly the pivaloyloxymethyl, acetoxymethyl, methoxymethyl, acetonyl, phenacyl, p-nitrobenzyl, $\beta,\beta,\beta$-trichloroethyl, 3-phthalidyl and 5-indanyl esters) thereof with an organic monocarboxylic acid chloride or a functional equivalent thereof as an acylating agent.

Such functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. In addition, an acid azide or an active ester or thioester (e.g. with p-nitrophenyl, 2,4-dinitrophenol, thiophenol, thioacetic acid) may be used or the free acid itself may be coupled with compound II after first reacting said free acid with N,N'-dimethylchloroforminimium chloride [cf. Great Britain 1,008,170 and Novak and Weichet, Experientia XXI, 6, 360 (1965)] or by the use of enzymes or of an N,N'-carbonyldiimidazole or an N,N'-carbonylditriazole [cf. South African patent specification No. 63/2684] or a carbodiimide reagent [especially N,N'-dicyclohexylcarbodiimide. N,N'-diisopropylcarbodiimide or N-cyclohexyl-N'-(2-morpholinoethyl)carbodiimide; cf. Sheehan and Hess, J. Amer. Chem. Soc., 77, 1967 (1955)], or of alkylylamine reagent [cf. R. Buijle and H. G. Viehe, Angew, Chem. International Edition 3, 582, (1964)] or of an isoxasolium salt reagent [cf. R. B. Woodward, R. A. Olofson and H. Mayer, J. Amer. Chem. Soc., 83, 1010 (1961)], or of a ketenimine reagent [cf. C. L. Stevens and M. E. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DPPA; J. Amer. Chem. Soc., 94, 6203-6205 (1972)] or of diethylphosphoryl cyanide [DEPC; Tetrahedron Letters No. 18, pp. 1595-1598 (1973)] or of diphenyl phosphite [Tetrahedron Letters No. 49, pp. 5047-5050 (1972)]. Another equivalent of the acid chloride is a corresponding azolide, i.e., an amide of the corresponding acid whose amide nitrogen is a member of a quasiaromatic five membered ring containing at least two nitrogen atoms, i.e., imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield dimidazolide. The by-product, imidazole, precipitates and may be separated and the imidazolide isolated, but this is not essential. The methods for carrying out these reactions to produce a cephalosporin and the methods used to isolate the cephalosporin so produced are well known in the art.

Mention was made above of the use of enzymes to couple the free acid with compound II. Included in the scope of such processes are the use of an ester, e.g. the methyl ester, of that free acid with enzymes provided by various micro-organisms, e.g. those described by T. Takahashi et al., J. Amer. Chem. Soc., 94(11), 4035-4037 (1972) and by T. Nara et al., J. Antibiotics (Japan) 24(5), 321-323 (1971) and in U.S. Pat. No. 3,682,777.

For the coupling of the organic carboxylic acid as described above with compound II (or a salt or preferably an easily hydrolyzed ester of Schiff base, as with benzaldehyde, thereof) it is also convenient and efficient to utilize as the coupling agent phosphonitrilic chloride trimer (J. Org. Chem., 33(7), 2979-81, 1968) or N-ethoxy-1,2-dihydroquinoline (EEDQ) as described in J. Amer. Chem. Soc., 90, 823-824 and 1652-1653 (1968) and U.S. Pat. No. 3,455,929. The reaction is preferably carried out at 30°-35° C. in benzene, ethanol or tetrahydrofuran using about equimolar quantities of all three reagents followed by conventional isolation and removal by conventional methods of any blocking groups present.

An additional process of the present invention comprises the preparation of the compounds of the present invention by the displacement of the 3-acetoxy group of a 7-acylaminocephalosporanic acid (prepared by substituting 7-aminocephalosporanic acid for the 3-thiolated-7-aminocephalosporanic acids in the acylation procedures described herein and elsewhere reported) with a thiol HSR$^3$ having the formula

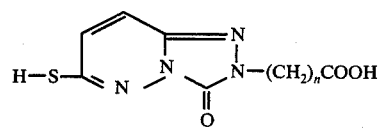

wherein n is 1 or 2 and then removing the protecting group if any is present, as on the carboxyl group.

The displacement of such a 3-acetoxy group with such a thiol may be accomplished in solution as in water or aqueous acetone at a temperature of at least room temperature and preferably within the range of about 50° to 100° C. in the presence of a mild base such as sodium bicarbonate, e.g. preferably near neutrality such as at about pH 6. An excess of the thiol is preferably employed. The reaction product is isolated by careful acidification of the reaction mixture followed by extraction with a water-immiscible organic solvent. As noted above, the preparation of many other 7-acylamidocephalosporanic acids is described in the patent and scientific literature, e.g. in U.S. Class 260-243C.

The salts of the compounds of this invention include the nontoxic carboxylic acid salts thereof, including non-toxic metallic salts such as sodium, potassium, calcium and aluminum, the ammonium salt and substituted ammonium salts, e.g. salts of such nontoxic amines as trialkylamines including triethylamine, procaine, dibenzylamine, N-benzyl-beta-phenethylamine, 1-ephenamine, N,N'-dibenzylethylenediamine, dehydroabietylamine, N,N'-bis-dehydroabietylethylenediamine, and other amines which have been used to form salts with benzylpenicillin, L-lysine, arginine and histidine.

The preferred esters of the cephalosporins of the present invention are the pivaloyloxymethyl, acetoxymethyl, methoxymethyl, acetonyl and phenacyl esters. All are useful intermediates in the production of the cephalosporin having a free carboxyl group.

As indicated above, these five esters of 7-aminocephalosporanic acid are each prepared by known methods. One excellent procedure is that of U.S. Pat. No. 3,284,451 in which sodium cephalothin is esterified by reaction with the corresponding active chloro or bromo compound (e.g. phenacyl bromide, chloroacetone, chloromethyl ether, pivaloyloxymethyl chloride [also called chloromethyl pivalate], acetoxymethyl chloride) and then the thienylacetic acid sidechain is removed enzymatically as in the same patent or chemically as in U.S. Pat. No. 3,575,970 and in Journal of Antibiotics, XXIV (11), 767–773 (1971). In another good method the triethylamine salt of 7-aminocephalosporanic acid is reacted directly with the active halogen compound, as in United Kingdom Pat. No. 1,229,453.

These esters of 7-aminocephalosporanic acid are then reacted with the nucleophile $HSR^3$ in the same manner as is illustrated herein for 7-aminocephalosporanic acid itself. The 3-thiolated ester of 7-aminocephalosporanic acid is then coupled with the organic carboxylic acid as before.

The ester of the cephalosporin so obtained is, if not used per se, converted to its free acid and, if desired, any salt by removal of the esterifying group, as by aqueous or enzymatic hydrolysis (as with human or animal serum) or acidic or alkaline hydrolysis or by treatment with sodium thiophenoxide as taught in U.S. Pat. No. 3,284,451 and, in the penicillin series, by Sheehan et al., J. Org. Chem. 29(7), 2006–2008 (1964).

In another alternative synthesis, the 3-thiolated 7-aminocephalosporanic acid is prepared as described herein and then acylated at the 7-amino group and finally esterified, as by reaction of the appropriate alcohol with the acid chloride prepared, for example, by reaction of the final cephalosporin with thionyl chloride or by other essentially acidic esterification procedures.

In the treatment of bacterial infections in man, the compounds of this invention are administered parenterally in an amount of from about 10 to 90 mg./kg./day and preferably about 14 to 50 mg./kg./day in divided dosage, e.g. two to four times a day. They are administered in dosage units containing, for example, 125, 250 or 500 mg. of active ingredient with suitable physiologically acceptable carriers or excepients. The dosage units are in the form of liquid preparations such as solutions or suspensions and preferably are aqueous solutions of a sodium or potassium salt which are injected intravenously or intramuscularly or by continuous or intermittent infusion in concentrations of about 125–500 mgm./ml., and preferably, 250 mgm./ml. as is customary in therapy with cephalosporin antibiotics.

STARTING MATERIALS

2-Furoylcyanide

To a suspension of 26.1 g. (0.4 mole) of ground potassium cyanide in 300 ml. of acetonitrile at 5° C. was added 26.1 g. (0.2 mole) of α-furoyl chloride while keeping the temperature below 8° C. The mixture was stirred in the cold for 15 minutes then heated at reflux for 30 minutes. The reaction was cooled, filtered and the acetonitrile was removed at 15 mm. (steam-bath) leaving 24.5 g. of a dark oil which was used without further purification. An infrared spectrum showed a nitrile band at 2265 $cm^{-1}$.

2-Furaneglyoxylic Acid

The 24.5 g. of crude 2-furoylcyanide was mixed with 160 ml. concentrated hydrochloric acid at 25° C. with intermittent stirring. The reaction was stored for 24 hours at 25° C. and diluted with 80 ml. of water. The reaction was stirred for 5 minutes and filtered. The filtrate was saturated with sodium chloride and extracted with 5 × 120 ml. of 1:1 ether-ethyl acetate solution. The extracts were combined, dried over anhydrous magnesium sulfate and evaporated at 30° C. (15 mm.) to give a brownish-orange solid. The solid was dissolved in methanol, treated with charcoal and evaporated under reduced pressure (15 mm.) to dryness to yield 17 g. of the acid.

The product was recrystallized from toluene to give 11.5 g. (m.p. 76° C.). The ir and nmr spectra were consistent for the structure.

2-Methoxyimino-2-furylacetic Acid

To a solution of 4.5 g. (0.032 mole) of 2-furaneglyoxylic acid in 40 ml. of 50% alcohol and 3.1 g. (0.037 mole) of methoxyamine hydrochloride in 6 ml. water at 20° C. was added dilute sodium hydroxide solution to pH 4–5. The solution was stirred at pH 4–5 at 25° C. for 24 hours. The alcohol was removed under reduced pressure (15 mm.) and the solution was adjusted to pH 7–8 with 50% sodium hydroxide solution. The reaction was extracted with 3 × 50 ml. of ether and the aqueous layer was adjusted to pH 1.9 using concentrated hydrochloric acid. The mixture was extracted with 5 × 50 ml. of ethyl acetate. The organic fractions were combined, washed with brine, dried over anhydrous magnesium sulfate and evaporated under reduced pressure (15 mm.) to an oil which was cooled for 1 hour in an ice bath. The product was slurried with Skellysolve B and collected to yield 3.1 g. of yellow crystals, m.p. 78° C. An analytical sample was recrystallized from toluene, dried for 16 hours in vacuo over $P_2O_5$ at 25° C. The ir and nmr spectra were consistent for the structure.

Anal. Calc'd for $C_7H_7NO$: C, 49.65; H, 4.17; N, 8.28. Found: C, 49.30; H, 4.21; N, 8.37.

2-Ethoxyiminofurylacetic Acid

The 7.85 g. (0.056 mole) of furyl-2-glyoxylic acid was dissolved in 100 ml. of water and adjusted to pH 7 with 50% sodium hydroxide. The 6.83 g. (0.070 mole) of ethoxyamine hydrochloride in 10 ml. of water was added, while keeping the pH at 4–5. The reaction was diluted with 25 ml. of alcohol, stirred 3 hours at room temperature and then filtered. The alcohol was removed at 35° C. (15 mm.) and the aqueous portion was adjusted with dilute sodium hydroxide solution to pH 7–8 and then was washed with ether and the washes were discarded. The aqueous fraction was adjusted with 6N hydrochloric acid to pH 1.5 and extracted into 3 × 80 ml. of ethyl acetate. The acetate fractions were combined, washed with brine and reduced in volume at 35° C. (15 mm.) to an oil. The oil was cooled in an ice bath, triturated with Skellysolve B, collected and dried over $P_2O_5$ in vacuo at 25° C. Yield: 4.8 g., m.p. 83°–85° C. The ir and nmr were consistent for the structure.

Anal. Calc'd for $C_8H_9NO_4$: C, 52.46; H, 4.95; N, 7.65. Found: C, 52.22; H, 4.94; N, 7.60.

Sodium α-Ethoxyimino-α-(2-furyl)acetate

To 50 ml. of methanol was added 250 mg. (0.0109 mole) of metallic sodium and stirred until all the sodium had dissolved. This sodium methoxide solution was treated with 2.0 g. (0.0109 mole) of α-ethoxyimino-α-(2-furyl)acetic acid dissolved in 10 ml. of methanol and stirred at room temperature for 1 hour. The methanol was removed at 40° C. (15 mm.) and the product was dried in vacuo over $P_2O_5$ at 25° C. to yield 2.22 g. white solid, m.p. decomp. >240° C. The ir and nmr were consistent for the structure.

"Skellysolve B" is a petroleum ether fraction of b.p. 60°–68° C. consisting essentially of n-hexane.

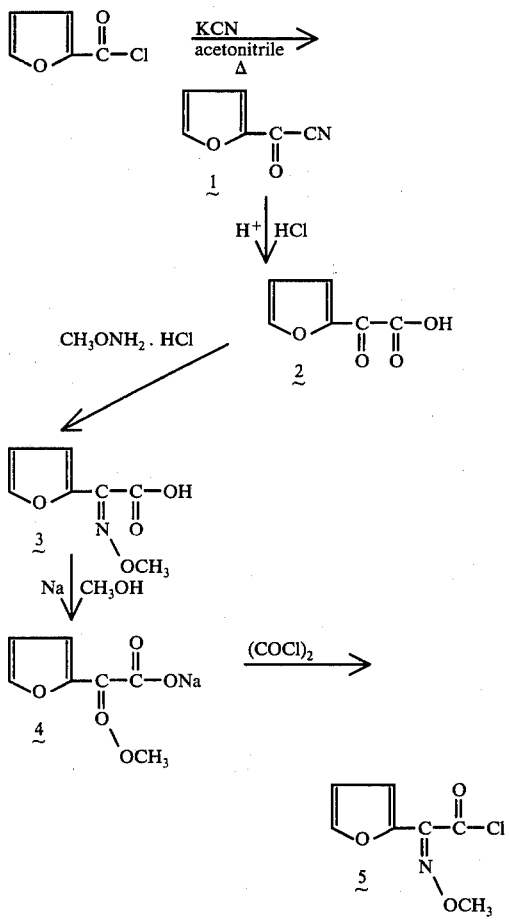

2-Furoylcyanide 1

To a suspension of 78.3 g. of powdered potassium cyanide in 900 ml. acetonitrile at 5° C. was added 59.25 ml. (68.5 g.) of α-furoyl chloride with vigorous stirring while keeping the temperature at 4°–8° C. The mixture was stirred at 4°–8° C. for 15 minutes and then heated at reflux for 30 minutes. The mixture was cooled to 23°–25° C., filtered, washed with 50 ml. of acetonitrile which was added to the filtrate, and the acetonitrile was removed at 60° C. (15 mm.) leaving 51 g. of 1 as a dark oil. An IR spectrum showed a nitrile band at 2265 $cm^{-1}$ and an NMR spectrum showed a ratio of approximately 70/30 of product 1/furoic acid. The crude product 1 was used without further purification (49% yield of product).

Furyl-2-glyoxylic Acid 2

The 51 g. of crude 2-furoyl cyanide 1 was mixed with 500 ml. concentrated hydrochloric acid at 25° C. The reaction was stirred for 24 hours at 25° C. and then diluted with 240 ml. of water. The mixture was stirred for 5 minutes and filtered. The black filtrate was saturated with sodium chloride and extracted with 6 × 500 ml. of 1:1 ether-ethyl acetate solution. (Note: Initially the extractions were difficult due to the inability to see the separation of two black phases. As additional ether-ethyl acetate extractions were run the task was simplified.) The extracts were combined and evaporated to dryness at 60° C. (15 mm.). The resultant solid was dissolved in 600 ml. ether, (Note: Use of alcohol should be avoided at this point as esters may form), treated with 10 g. of charcoal ("Darko-KB"), filtered after stirring for 0.5 hour and evaporated to dryness at 50° C. (15 mm.) to yield 46.6 g. of 2 as a light tan colored acid. This product 2 was found to contain a ratio of approximately 56/44 of product 2/furoic acid. This represented a 63% yield of product 2.

Purification was accomplished by dissolving the above crude product 2 in $H_2O$ (50 mg./ml.), titrating to pH 2.8 with HCl and extracting with 2 × 200 ml. of ethyl acetate. Evaporation of the ethyl acetate extracts gave 35% furoic acid and 15% product 2. The pH 2.8 aqueous phase was adjusted to pH 0.8 (HCl) and extracted with 2 × 200 ml. ethyl acetate. The organic extracts were combined and washed with 50 ml. $H_2O$. The organic phase was evaporated at 50° C. (15 mm.) yielding a solid with a ratio of approximately 86/14 of product 2/furoic acid. This solid was then recrystallized by dissolving the product 2 in toluene at 50 mg./ml. at 80° C., decanting, and leaving to crystallize at room temperature for 18 hours, yielding 13.3 g. of pure acid 2 by NMR. This represented a 51% yield in the purification and recrystallization step and an overall yield from the 2-furoyl chloride to the pure furyl-2-glyoxylic acid 2 of 16%.

Syn-α-methoxyiminofurylacetic Acid 3

A solution of 4.5 g. of furyl-2-glyoxylic acid 2 in 40 ml. of 50% ethanol was titrated to pH 6 with 1N sodium hydroxide and then 3.1 g. of methoxyamine.HCl in 6 ml. of $H_2O$ at 20° C. was added. The solution was titrated to a constant pH 4.9 and stirred at pH 4.9 for 24 hours at 20°–23° C. The ethanol was then removed at 50° C. (15 mm.) and the residual aqueous solution was titrated to pH 8 with 50% sodium hydroxide and washed with 3 × 50 ml. ether (pH adjusted to 8 after each wash). The aqueous layer was titrated to pH 1.9 with concentrated HCl and extracted with 5 × 50 ml. ethyl acetate with the pH readjusted to 1.9 after each extraction. The ethyl acetate extracts were combined and evaporated to a solid 3 at 50° C. (15 mm.). This solid was then slurried with 75 ml. of "Skellysolve B". The suspension was filtered and the solids were redissolved in 16 ml. of toluene at 80° C. The hot solution was decanted and left to crystallize at 20°–23° C. for 18 hours to yield 1.17 g. 3 (22% yield of product). The NMR was clean and consistent for the structure 3 with a trace of anti isomer present.

Sodium Syn-α-methoxyiminofurylacetate 4

To 40 ml. of methanol was added 0.16 g. of sodium. The mixture was stirred until all of the sodium dissolved and then decanted. The resulting sodium methoxide solution was cooled to 3° C. and 1.12 g. of syn-α-methoxyiminofurylacetic acid 3 in 7.8 ml. of methanol was added. The solution was stirred for 10 minutes at room temperature. The solvent was evaporated at 40° C. (15 mm.). The residue 4 was dried by azeotropic distillation with 3 × 20 ml. of benzene at 40° C. (15 mm.). The product 4 was dried for 18 hours at 23° C. under high vacuum (0.7 mm.) over $P_2O_5$ yielding 1.25 g. (99% yield of product). The NMR showed this product 4 to be clean and consistent for the structure with 0.15 mole methanol and a trace of anti isomer.

To 0.63 g. of sodium syn-α-methoxyiminofurylacetate 4 suspended in 25 ml. of benzene was added four drops of dry dimethylformamide and 0.31 ml. (1.1 eq.) of oxalyl chloride. This mixture was stirred for 40 minutes at 20°–23° C. The benzene was removed at 35° C. (15 mm.) to provide the acid chloride 5 as the gummy residue.

6-Chloro-2,3-dihydro-2-ethoxycarbonylmethyl-s-triazolo[4,3-b]pyridazin-3-one

To a solution of 6-chloro-2,3-dihydro-s-triazolo[4,3-b]pyridazin-3-one [P. Francavilla and F. Lauria, J. Het. Chem., 8, 415 (1971)] (1, 1.00 g., 5.9 m.mole) in dry DMF (30 ml.) was added sodium hydride (50% in paraffin, 0.3 g., 6.3 m.mole) under stirring with formation of yellow crystals. To the mixture was added ethyl chloroacetate (1.4 ml., 13 m.mole) and the mixture was heated at 90° C. for 8 hours with stirring. After cooling, the reaction mixture was poured into water (50 ml.) and extracted with toluene (5 × 40 ml.). The organic extracts were combined, dried over anhydrous sodium sulfate and evaporated at reduced pressure. The residue was crystallized with benzene-n-hexane to give yellow needles (1.16 g., 77%), m.p. 114°–115° C. (lit. 110° C.).

ir: $\nu_{max}^{KBr}$ 1735, 1710 cm$^{-1}$.
uv: $\lambda_{max}^{EtOH}$ 231 nm (ε, 26000)
nmr: $\delta_{ppm}^{CDCl_3}$ 7.58 (1H, d, J=10 Hz, pyridazine-H), 6.98 (1H, d, J=10 Hz, pyridazine-H), 4.80 (2H, s, —CH$_2$CO), 4.27 (2H, q, J=7.5 Hz, CH$_2$CH$_3$), 1.29 (3H, t, J=7.5 Hz, CH$_2$CH$_3$).
Anal. Calc'd. for $C_9H_9N_4O_3Cl$: C, 42.12; H, 3.53; N, 21.83; Cl, 13.81. Found: C, 41.54, 41.46; H, 3.22, 3.49; N, 21.51, 21.53; Cl, 13.88, 13.99.

2-Carboxymethyl-2,3-dihydro-6-mercapto-s-triazolo[4,3-b]pyridazin-3-one

To a solution of 6-chloro-2,3-dihydro-2-ethoxycarbonylmethyl-s-triazolo[4,3-b]pyridazin-3-one (30 g., 0.12 mole) in ethanol (900 ml.) was added NaSH.2H$_2$O (70% pure, 45.9 g., 0.36 mole) and the mixture was refluxed for 0.5 hour. The reaction mixture was evaporated at reduced pressure. The residue was dissolved in water (200 ml.) and concentrated HCl was added to the solution to adjust to pH 2. The precipitate of 2-carboxymethyl-2,3-dihydro-6-mercapto-s-triazolo[4,3-b]pyridazin-3-one was collected by filtration and washed with water. Yield 18.3 g. (69%).

ir: $\nu_{max}^{KBr}$ 2900, 2450, 1750, 1660 cm$^{-1}$.

uv: $\lambda_{max}^{1\% NaHCO_3 aq.}$ 260 nm (ε,19500), 313 nm (ε, 7000)
nmr: $\delta_{ppm}^{DMSO-d_6}$ 7.88 (1H, d, J=10 Hz, pyridazine-H), 7.45 (1H, d, J=10 Hz, pyridazine-H), 4.72 (2H, s, CH$_2$CO).
Anal. Calc'd. for $C_7H_6N_4O_3S$: C, 37.17; H, 2.67; N, 24.77; S, 14.17. Found: C, 37.35, 37.23; H, 2.26, 2.28; N, 23.58, 23.69; S, 14.32.

7-Amino-3-(2-carboxymethyl-2,3-dihydro-s-triazolo[4,3-b]pyridazin-3-on-6-ylthiomethyl)-3-cephem-4-carboxylic Acid To a suspension of 7-aminocephalosporanic acid (8.79 g., 32.2 m.mole) in 0.1 M phosphate buffer (pH 7, 149 ml.) were added NaHCO$_3$ (8.14 g., 97.0 m.mole) and the thiol 2-carboxymethyl-2,3-dihydro-6-mercapto-s-triazolo[4,3-b]pyridazin-3-one (7.30 g., 32.2 m.mole) with stirring. The mixture was heated at 80° C. for 0.5 hour under N$_2$ stream. The mixture was treated with active carbon and adjusted to pH 3 with concentrated HCl. The resulting precipitate was collected by filtration and washed with water to give 7.59 g. (54%) of 7-amino-3-(2-carboxymethyl-2,3-dihydro-s-triazolo[4,3-b]pyridazin-3-on-6-ylthiomethyl)-3-cephem-4-carboxylic acid.

ir: $\nu_{max}^{KBr}$ 1800, 1720, 1600, 1540, 1470 cm$^{-1}$.
uv: $\lambda_{max}^{Buffer}$ (pH 7) 252 nm (ε,19500), 298 nm (ε, 8400).
nmr: $\delta_{ppm}^{D_2O+K_2CO_3}$ 7.56 (1H, d, J=9 Hz, pyridazine-H), 7.05 (1H, d, J=9 Hz, pyridazine-H), 5.45 (1H, d, J=5 Hz, 6-H), 5.05 (1H, d, 5 Hz, 7-H), 4.43 (1H, d, J=14 Hz, 3-CH$_2$), 4.04 (1H, d, J=14 Hz, 3-CH$_2$), 3.88 (1H, d, J=18 Hz, 2-H), 3.45 (1H, d, J=18 Hz, 2-H).

6-Chloro-2-(2-cyanoethyl)-2,3-dihydro-s-triazolo[4,3-b]pyridazin-3-on

To a solution of 6-chloro-2,3-dihydro-s-triazolo[4,3-b]pyridazin-3-on [P. Francabilla and F. Lauria, J. Het. Chem. 8, 415 (1971)] (17 g., 0.1 .mole) in dry DMF (300 ml.) was added potassium tert.-butoxide (0.5 g., 4.5 m.moles) with stirring. Acrylonitrile (6.6 g., 0.12 .mole) in dry DMF (10 ml.) was added to the mixture. The mixture was stirred at 100°–110° C. for 24 hours, then poured into water (700 ml.) and extracted with ethyl acetate (5 × 400 ml.). The organic extracts were combined, dried over Na$_2$SO$_4$ and evaporated. The residue was crystallized from ethyl acetate to give light yellow needles of 6-chloro-2-(2-cyanoethyl)-2,3-dihydro-s-triazolo[4,3-b]pyridazin-3-on (2.5 g., 11%). M.p. 166°–168° C.

ir: $\nu_{max}^{KBr}$ 2230, 1720, 1550, 1500 cm$^{-1}$.
uv: $\lambda_{max}^{dioxane}$ 373 nm (ε 2000).
nmr: $\delta_{ppm}^{DMSO-d_6}$ 3.03 (2H, t, J=6.0 Hz, CH$_2$), 4.21 (2H, t, J=6.0 Hz, CH$_2$), 7.23 (1H, d, J=10.0 Hz, pyridazine-H), 7.93 (1H, d, J=10.0 Hz, pyridazine-H).
Anal. Calc'd, for $C_8H_6N_5OCl$: C, 42.97; H, 2.70; N, 31.32; Cl, 15.86. Found: C, 42.73, 42.56; H, 2.57, 2.50; N, 31.36, 31.68; Cl, 15.96, 15.81.

2-(2-Carboxyethyl)-6-chloro-2,3-dihydro-s-triazolo[4,3-b]pyridazin-3-on

A solution of 6-chloro-2-(2-cyanoethyl)-2,3-dihydro-s-triazolo[4,3-b]pyridazin-3-on (724 mg.) in 6N—HCl (15 ml.) was refluxed for 6 hours. The reaction mixture was extracted with ethyl acetate (10 × 20 ml.). The combined extracts were washed with saturated aqueous sodium chloride (50 ml.), dried over Na$_2$SO$_4$ and evaporated to give light yellow, solid 2-(2-carboxyethyl)-6- chloro-2,3-dihydro-s-triazolo[4,3-b]pyridazin-3-on (567 mg., 72%). M.p. >170° C. (sublimation).

ir: $\nu_{max}^{KBr}$ 3400–2400, 1730, 1710, 1540 cm$^{-1}$.

uv: $\lambda_{max}^{dioxane}$ 377 nm ($\epsilon$ 1500).

nmr: $\delta_{ppm}^{D_2O+NaHCO_3}$ 2.70 (2H, t, J=7.0 Hz, C$\underline{H}_2$), 4.24 (2H, t, J=7.0 Hz, C$\underline{H}_2$), 7.17 (1H, d, J=10.0 Hz, pyridazine-H), 7.70 (1H, d, J=10.0 Hz, pyridazine-H).

Anal. Calc'd. for $C_8H_7N_4O_3Cl$: C, 39.60; H, 2.91; N, 23.09; Cl, 14.61. Found: C, 39.62, 39.48; H, 2.97, 2.67; N, 23.05, 22.70; Cl. 13.93, 14.12.

2-(2-Carboxyethyl)-2,3-dihydro-6-mercapto-s-triazolo[4,3-b]pyridazin-3-on

A mixture of 2-(2-carboxyethyl)-6-chloro-2,3-dihydro-s-triazolo[4,3-b]pyridazin-3-on (567 mg., 2.34 m.moles) and 70% sodium hydrosulfide dihydrate (924 mg., 7.02 m.mole) in water (10 ml.) was stirred at room temperature for 2 hours. The reaction mixture was adjusted successively to pH 1 with c. HCl, to pH 10 with NaOH and then to pH 1 with c. HCl. The resulting precipitate of 2-(carboxyethyl)-2,3-dihydro-6-mercapto-s-triazolo[4,3-b]pyridazin-3-on was collected by filtration and washed with water. Yield: 418 mg. (74%). M.p. 174°–176° C.

ir: $\nu_{max}^{KBr}$ 3600–2600, 2440, 1730, 1720 (sh) cm$^{-1}$.

uv: $\lambda_{max}^{pH\ 7\ buffer}$ 262 nm ($\epsilon$ 17000), 318 nm ($\epsilon$ 6600).

nmr: $\delta_{ppm}^{DMSO-d_6}$ 2.73 (2H, t, J=7.0 Hz, C$\underline{H}_2$), 4.07 (2H, t, J=7.0 Hz, C$\underline{H}_2$), 7.30 (1H, d, J=10.0 Hz, pyridazine-H), 7.74 (1H, d, J=10.0 Hz, pyridazine-H).

Anal. Calc'd. for $C_8H_8N_4O_3S$: C, 40.00; H, 3.36; N, 23.32; S, 13.35. Found: C, 39.08, 39.06; H, 3.12, 3.20; N, 22.65, 22.70; S, 14.23, 14.29.

7-Amino-3-[2-(2-carboxyethyl)-2,3-dihydro-s-triazolo[4,3-b]pyridazin-3-on-6-ylthiomethyl]-3-cephem-4-carboxylic Acid A mixture of 7-ACA (405 mg., 1.49 m.moles), the thiol 2-(2-carboxyethyl)-2,3-dihydro-6-mercapto-s-triazolo[4,3-b]pyridazin-3-on (357 mg., 1.49 m.moles) and NaHCO$_3$ (375 mg., 4.47 m.moles) in 0.1 M phosphate buffer (pH 7, 8 ml.) was stirred at 80° C. for 30 minutes. The reaction mixture was cooled and filtered to remove insolubles. The filtrate was adjusted to pH 1-2 with c. HCl. The resulting precipitate, 7-amino-3-[2-(2-carboxyethyl)-2,3-dihydro-s-triazolo[4,3-b]pyridazin-3-on-6-ylthiomethyl]-3-cephem-4-carboxylic acid, was collected by filtration and washed with water. Yield: 519 mg. (77%).

ir: $\nu_{max}^{KBr}$ 3600–2200, 1800, 1725, 1620, 1550, 1480 cm$^{-1}$.

uv: $\lambda_{max}^{pH\ 7\ buffer}$ 253 nm ($\epsilon$ 20000), 298 nm ($\epsilon$ 10000).

nmr: $\delta_{ppm}^{D_2O+K_2CO_3}$ 2.20 (2H, t, J=7.0 Hz, C$\underline{H}_2$), 3.40 (1H, d, J=17.5 Hz, 2-H), 3.85 (1H, d, J=17.5 Hz, 2-H), 4.00–4.50 (4H, m, 3-C$\underline{H}_2$ and N—C$\underline{H}_2$—), 5.01 (1H, d, J=4.0 Hz, 6-H), 5.40 (1H, d, J=4.0 Hz, 7-H), 6.94 (1H, d, J=10.0 Hz, pyridazine-H), 7.44 (1H, d, J=10.0 Hz, pyridazine-H).

Anal. Calc'd. for $C_{16}H_{16}N_6O_6S_2.3/2H_2O$: C, 40.09; H, 3.99; N, 17.52; S, 13.37. Found: C, 40.06, 40.12; H, 3.33, 3.34; N, 16.96, 16.98; S, 13.87, 13.98.

7-ACA refers to 7-aminocephalosporanic acid and DMF to dimethylformamide.

DESCRIPTION OF THE PREFERRED EMBODIMENTS

EXAMPLE 1

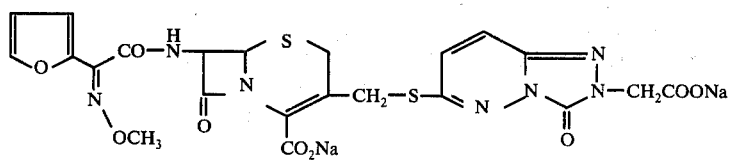

7-[(2Z)-2-Methoxyimino(fur-2-yl)acetamido]-3-(2-carboxymethyl-2,3-dihydro-s-triazolo[4,3-b]pyridazin-3-on-6-ylthiomethyl)-3-cephem-4-carboxylic Acid Disodium Salt; BB-S511

To a solution of (2Z)-2-methoxyimino(fur-2-yl)acetic acid (507 mg., 3 m.moles) and triethylamine (0.42 ml., 3 m.moles) in dichloromethane (6 ml.) was added oxyalyl chloride (0.26 ml., 3 m.moles) at 0°–5° C. and the mixture was stirred for 30 minutes. The mixture was evaporated at reduced pressure to give an oily residue of the acid chloride which was dissolved in dry acetone (10 ml.). After filtration the acetone solution was added to a mixture of 7-amino-3-(2-carboxymethyl-2,3-dihydro-s-triazolo[4,3-b]pyridazin-3-on-6-ylthiomethyl)-3-cephem-4-carboxylic acid (1.31 g., 3 m.moles) and NaHCO$_3$ (504 mg., 6 m.moles) in water (20 ml.) at 0°–5° C. The mixture was stirred at 0°–5° C. for 2 hours with the acetone being removed under reduced pressure. The aqueous solution was washed with ether (2 × 50 ml.) and adjusted to pH 1-2 with conc. HCl to afford a precipitate which was collected by filtration, washed with water and dried in vacuo. The solid was dissolved in THF (tetrahydrofuran) (40 ml.) and filtered. To the filtrate was added 1 M-SEH (sodium ethylhexanoate) in ethyl acetate (3 ml.) and the resulting precipitate was collected by filtration and dried in vacuo. Yield of 7-[(2Z)-2-methoxyimino(fur-2-yl)acetamido]-3-(2-carboxymethyl-2,3-dihydro-s-triazolo[4,3-b]pyridazin-3-on-6-ylthiomethyl)-3-cephem-4-carboxylic acid disodium salt was 1.0 g. (54%) mp >210° C. (dec.).

ir: $\nu_{max}^{KBr}$ 1770, 1710, 1680, 1610, 1550 cm$^{-1}$.

uv: $\lambda_{max}^{pH\ 7\ buffer}$ 257 nm ($\epsilon$ 25000), 277 nm ($\epsilon$ 24000).

nmr: $\delta_{ppm}^{DMSO-d_6}$ 7.70 (1H, br, furan-H$\alpha$), 7.52 (1H, d, J=9.5 Hz, pyridazine-H), 6.87 (1H, d, J=9.5 Hz, pyridazine-H), 6.5–6.6 (2H, m, furan-H$\beta$), 5.58 (1H, m, 7-H), 5.00 (1H, d, J=4.5 Hz, 6-H), 3.84 (3H, s, OC$\underline{H}_3$).

Anal. Calc'd. for $C_{22}H_{17}N_7O_9S_2Na_2.H_2O$: C, 40.55; H, 2.94; N, 15.05; S, 9.84. Found: C, 40.81, 41.02; H, 3.08, 3.22; N, 14.69, 14.86; S, 9.70, 9.62.

EXAMPLE 2

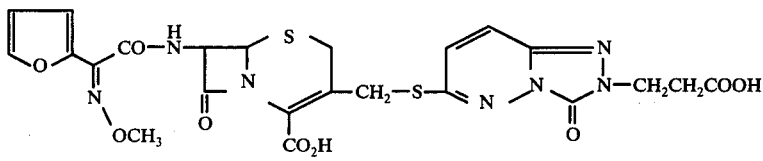

7-[(2Z)-2-Methoxyimino(fur-2-yl)acetamido]-3-[2-(2-carboxyethyl)-2,3-dihydro-s-triazolo[4,3-b]pyridazin-3-on-6-ylthiomethyl]-3-cephem-4-carboxylic Acid Sodium Salt; BB-S526

The acid chloride prepared from (2Z)-2-methoxyimino(fur-2-yl)acetic acid (169 mg., 1 m.mole) was dissolved in dry acetone (5 ml.) and filtered to remove insolubles. The filtrate was added to a solution of 7-amino-3-[2-(2-carboxyethyl)-2,3-dihydro-s-triazolo[4,3-b]pyridazin-3-on-6-ylthiomethyl]-3-cephem-4-carboxylic acid, (452 mg., 1 m.mole) and NaHCO₃ (336 mg., 4 m.mole) in water (10 ml.). The reaction mixture was stirred for 2 hours in an ice-water bath. Acetone was removed at reduced pressure. The aqueous solution was washed with ether (2 × 10 ml.) and adjusted to pH 1–2 with conc. HCl. The resulting precipitate was collected by filtration, washed with water and dried under reduced pressure. A solution of the precipitate in THF (10 ml.) was treated with active carbon. A SEH solution in ethyl acetate (1 M, 0.8 ml.) was added to the THF solution to give 7-[(2Z)-2-methoxyimino(fur-2-yl)acetamido]-3-[2-(2-carboxyethyl)-2,3-dihydro-s-triazolo[4,3-b]pyridazin-3-on-6-ylthiomethyl]-3-cephem-4-carboxylic acid sodium salt which was collected by filtration. Yield: 410 mg. (66% as mono Na salt). Mp. >205° C. (dec.).

ir: $\nu_{max}^{KBr}$ 3600–2800, 1770, 1710, 1600, 1550 cm$^{-1}$.

uv: $\lambda_{max}^{pH\ 7\ buffer}$ 257 nm ($\epsilon$ 27000), 276 ($\epsilon$ 26100).

nmr: $\delta_{ppm}^{DMSO\text{-}d_6 + D_2O}$ 2.70 (2H, t, J=6 Hz, C$\underline{H}_2$), 3.3–4.5 (9H, m, 2-H, 3-C$\underline{H}_2$, CH$_2$ and OC$\underline{H}_3$), 4.96 (1H, d, J=5.5 Hz, 6-H), 5.53 (1H, d, J=5.5 Hz, 7-H), 6.55 (2H, m, furan-H), 6.92 (1H, d, J=10 Hz, pyridazine-H), 7.53 (1H, d, J=10 Hz, pyridazine-H), 7.68 (1H, br, furan-H).

Anal. Calc'd. for C₂₃H₂₀N₇O₉S₂Na·H₂O: C, 42.92; H, 3.45; N, 15.23; S, 9.96. Found: C, 43.08, 42.77; H, 3.20, 3.03; N, 14.96, 14.76; S, 9.96.

TABLE 1
In vitro Activity Using Mueller-Hinton Agar By the Serial Dilution Method

|  | Geometric Mean of MIC (Mcg./ml.) | | |
|---|---|---|---|
|  | BB-S511 (Ex. 1) | BB-S526 (Ex. 2) | Cefuroxime |
| S. aureus (3 strains) | 1.97 | 1.6 | 1.24 |
| E. coli (7) | 0.58 | 0.78 | 1.28 |
| Kl. pneumoniae (4) | 0.47 | 0.93 | 3.1 |
| Proteus (6) | 0.021 | 0.061 | 0.88 |
| Shig. (3), Serr. (1) (1), Sal. (2) | 1.11 | 2.41 | 4.06 |
| B. anthracis (1) |  |  |  |
| S. pyrogenes (5) | 0.032 | 0.032 | 0.025 |
| S. viridans (5) | 0.15 | 0.4 | 0.1 |
| D. pneumoniae (5) | 0.037 | 0.056 | 0.0125 |
| N. meningitidis (5) | 2.37 | 3.60 | 1.6 |
| N. gonorrhoeae (5) | 1.36 | 1.6 | 0.4 |
| H. influenzae (7) | 0.64 | 0.71 | 1.16 |

Cefuroxime is sodium 6R,7R-3-carbamoyloxymethyl-7-(2Z)-2-methoxyimino(fur-2-yl)acetamidoceph-3-em-4-carboxylate.

TABLE 2
Geometric Means of MIC's Against 3 Strains of S. aureus and 27 Strains of Gram-negative Bacteria (mcg./ml., Mueller-Hinton Agar)

|  | No. of Strains | BB-S511 | BL-S786 |
|---|---|---|---|
| S. aureus | 1 | 1.6 | 1.6 |
| S. aureus, Penicillin-R | 2 | 0.6 | 1.6 |
| E. coli | 6 | 0.2 | 0.2 |
| E. coli, Cephalosporin-R | 1 | 6.3 | 12.5 |
| K. pneumoniae | 4 | 0.7 | 0.3 |
| Indole (−) Proteus | 2 | 0.1 | 0.2 |
| Indole(+) Proteus | 3 | 0.05 | 0.3 |
| Indole(+) Proteus, Cephalosporin-R | 2 | 6.3 | 50.1 |
| S. marcescens | 1 | 25 | >100 |
| E. cloacae | 1 | 3.1 | 1.6 |
| Shigella, Salmonella | 5 | 0.3 | 0.5 |
| P. aeruginosa | 2 | >100 | >100 |

BL-S786 is 7-[α-(2-aminomethylphenyl)acetamido]-3-[(1-carboxymethyltetrazol-5-ylthio)methyl]-3-cephem-4-carboxylic acid.

TABLE 3
Geometric Means of MIC's Against 18 Strains of S. marcescens

| BB-S511 | BL-S786 |
|---|---|
| 5.4 | 85.9 |

EXAMPLE 3

Substitution of an equimolar weight of 3-ethoxyimino-2-(fur-2-yl)acetic acid for the 2-methoxyiminofuryl acetic acid used in the procedures of Examples 1 and 2 produces 7-(2-ethoxyimino-2-furylacetamido)-3-(2-carboxymethyl-2,3-dihydro-s-triazolo[4,3-b]pyridazin-3-on-6-ylthiomethyl)-3-cephem-4-carboxylic acid and 7-(2-ethoxyimino-2-furylacetamido)-3-[2-(2-carboxyethyl)-2,3-dihydro-s-triazolo[4,3-b]pyridazin-3-on-6-ylthiomethyl]-3-cephem-4-carboxylic acid, respectively.

EXAMPLE 4

Substitution of an equimolar weight of 2-n-propoxyimino-2-(fur-2-yl)acetic acid for the 2-methoxyiminofuryl acetic acid used in the procedures of Examples 1 and 2 produces 7-(2-n-propoxyimino-2-furylacetamido)-3-(2-carboxymethyl-2,3-dihydro-s-triazolo[4,3-b]pyridazin-3-on-6-ylthiomethyl)-3-cephem-4-carboxylic acid and 7-(2-n-propoxyimino-2-furylacetamido)-3-[2-(2-carboxyethyl)-2,3-dihydro-s-triazolo[4,3-b]pyridazin-3-on-6-ylthiomethyl]-3-cephem-4-carboxylic acid, respectively.

EXAMPLE 5

Substitution of an equimolar weight of 2-n-butoxyimino-2-(fur-2-yl)acetic acid for the 2-methoxyiminofuryl acetic acid used in the procedures of Examples 1 and 2 produces 7-(2-n-butoxyimino-2-furylacetamido)-3-(2-carboxymethyl-2,3-dihydro-s-triazolo[4,3-b]pyridazin-3-on-6-ylthiomethyl)-3-cephem-4-carboxylic acid and 7-(2-n-butoxyimino-2-furylacetamido)-3-[2-(2-carboxyethyl)-2,3-dihydro-s- triazolo[4,3-b]pyridazin-3-on-6-ylthiomethyl]-3-cephem-4-carboxylic acid, respectively.

EXAMPLE 6

The products of Examples 1–5 are prepared as syn isomers essentially free of the corresponding anti isomers by the use in the procedures of those examples of purified syn isomers of the appropriate 2-alkoxyimino-2-(fur-2-yl)acetic acid. Conversion of part of the syn isomer to anti isomer during preparation of the acid chloride from the acid is substantially avoided by minimizing its exposure to hydrogen chloride, e.g. by first converting the acid to its anhydrous sodium salt and by treating that salt with oxalyl chloride under anhydrous conditions in the presence of a hydrogen ion acceptor such as dimethylformamide.

Such syn isomers are also named as (2Z)-2-alkoxyimino-2-(fur-2-yl)acetic acids.

EXAMPLE 7

An injectable pharmaceutical composition is formed by adding sterile water or sterile saline solution (2 ml.) to 100–500 mgm. of 7-[(2Z)-2-methoxyimino(fur-2-yl)acetamido]-3-(2-carboxymethyl-2,3-dihydro-s-triazolo[4,3-b]pyridazin-3-on-6-ylthiomethyl)-3-cephem-4-carboxylic acid disodium salt.

Pharmaceutical compositions of the sodium and potassium salts of the other compounds of the present invention, preferably in the form of the pure syn isomer, are formulated in a similar manner.

When the compounds are first prepared in the form of the free acid they are converted to the desired, highly water soluble potassium salt by treatment with potassium 2-ethylhexanoate using the procedure of Example 1.

It is occasionally advantageous to have admixed with said solid cephalosporin as a stabilizing and/or solubilizing agent a sterile, anhydrous solid such as sodium carbonate, potassium carbonate or lithium carbonate (e.g. in about 5 or 6 percent by weight of the weight of the cephalosporin) or such as L-lysine, arginine or histidine (e.g. in about 20–50% by weight of the weight of the cephalosporin) or such as a sodium, potassium or calcium salt of levulinic acid, citric acid, ascorbic acid, tartaric acid or pyruvic acid (e.g. in about 25–200% by weight of the weight of the cephalosporin) or such as sodium bicarbonate, ammonium carbamate alkali metal or ammonium phosphates or N-methylglucamine (per U.K. Pat. No. 1,380,741).

There is also provided by the present invention a compound having the formula

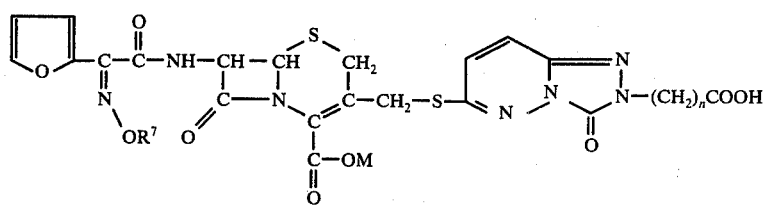

wherein $R^7$ is alkyl containing 1–4 carbon atoms, $n$ is 1 or 2 and M is $$M \text{ is } -\underset{R^1}{\text{CHO}}\overset{O}{\overset{\|}{C}}(CH_2)_n R, \; -\underset{R^1}{\text{CHO}}\overset{O}{\overset{\|}{C}}(CH_2)_n C \underset{NR^4R^5}{\overset{R^3}{\diagdown}},$$

$$-\underset{R^1}{\text{CHXCOR}^6} \text{ or } -\underset{R^1}{\text{CH}}-S-\overset{O}{\overset{\|}{C}}-R^6$$

$n$ is 0 to 4; R is hydrogen, alkyl having 1 to 8 carbon atoms, cycloalkyl of 3 to 6 carbon atoms, phenyl, $C_1$–$C_4$ phenalkyl, pyridyl, thienyl, or propyl; $R^1$ is hydrogen, methyl or ethyl; $R^2$ and $R^3$ are each hydrogen, alkyl having 1 to 6 carbon atoms, phenyl, pyridyl, or thienyl; $R^4$ and $R^5$ are each hydrogen or alkyl of 1 to 4 carbon atoms; $R^6$ is alkyl having 1 to 4 carbon atoms, phenyl, phenalkyl having 1 to 4 carbon atoms, pyridyl, thiadiazolyl, amino or $C_1$–$C_4$ alkylamino; X is NH or oxygen; and each phenyl group is unsubstituted or substituted with one or two substituents selected from the group consisting of alkyl having 1 to 6 carbon atoms, alkoxy having 1 to 4 carbon atoms, hydroxy, amino, $NHR^1$, $N(R^1)_2$, nitro, fluoro, chloro, bromo or carboxy, or a nontoxic, pharmaceutically acceptable salt thereof, said compound being at least 75% by weight in the form of its syn isomer and preferably in the form of its syn isomer essentially free of the corresponding anti isomer.

There is also provided by the present invention a compound having the formula

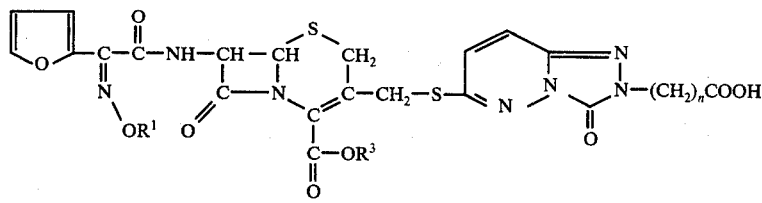

wherein $R^1$ is alkyl containing 1–4 carbon atoms, $n$ is 1 or 2 and $R^3$ is selected from the group consisting of $$\underset{-\text{CH}-\text{O}-\overset{\|}{C}-R^6}{\overset{CH_3}{|}}\overset{O}{\overset{\|}{,}} \; \underset{-\text{CH}-\overset{\|}{C}-R^6}{\overset{C_2H_5}{|}}\overset{O}{\overset{\|}{,}} \; \underset{-\text{CH}-X^2-\overset{\|}{C}-OR^7}{\overset{R^5}{|}}\overset{O}{\overset{\|}{,}}$$

wherein $R^5$ is a hydrogen atom, a methyl or an ethyl group; $X^2$ is —O—, —NH—; $R^6$ is a basic group such as alkyl or aralkyl substituted with substituted or unsubstituted $NH_2$, such as alkyl-$NHCH_3$, aralkyl-$NHCH_3$,

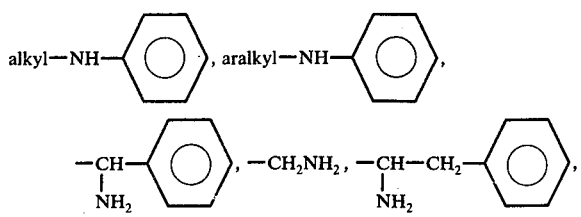

$R^7$ is an alkyl group such as a methyl, ethyl, propyl, isopropyl, butyl, isobutyl, pentyl or 2-ethyl-hexyl group; a cycloalkyl group such as cyclopropyl, cyclobutyl, cyclopentyl, cyclohexyl or cycloheptyl; an aryl group such as phenyl or naphthyl; an aralkyl group such as benzyl or naphthylmethyl; a heterocyclic group and wherein the alkyl, cycloalkyl, aryl, aralkyl and heterocyclic groups may be substituted with one or more groups selected from the class consisting of amino groups, substituted amino groups such as methylamino, diethylamino or acetamido groups, the halogen groups such as fluorine, chlorine or bromine, nitro groups, alkoxy groups such as methoxy, ethoxy, propyloxy, isopropyloxy, butoxy or isobutoxy; or a nontoxic pharmaceutically acceptable salt thereof, said compound being at least 75% by weight in the form of its syn isomer and preferably in the form of its syn isomer especially free of the corresponding anti isomer.

There is also provided by the present invention a compound having the formula

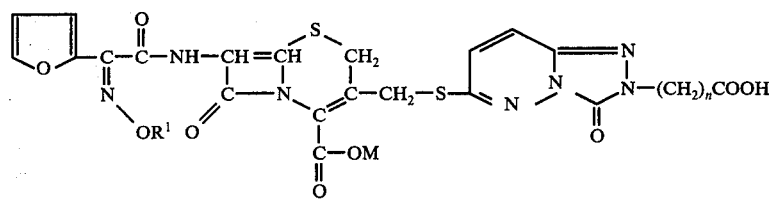

wherein $R^1$ is alkyl containing 1-4 carbon atoms, $n$ is 1 or 2 and M is

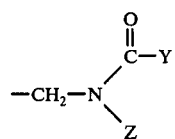

wherein Y is alkyl of one to six carbon atoms, phenyl, benzyl, alkoxy of one to six carbon atoms, or benzyloxy; Z is alkyl of one to six carbon atoms, phenylbenzyl, alkoxy of one to six carbon atoms, cyclopentyl, cyclohexyl and phenyl, or Y+Z taken together are a 3-benzoxazolidine ring; or a nontoxic, pharmaceutically acceptable salt thereof, said compound being at least 75% by weight in the form of its syn isomer and preferably in the form of its syn isomer essentially free of the corresponding anti isomer.

Also included within the present invention are pharmaceutical compositions comprising a mixture of an antibacterially effective amount of a compound of the present invention and a semisynthetic penicillin or another cephalosporin or a cephamycin or a β-lactamase inhibitor or an aminoglycoside antibiotic.

There is further provided by the present invention a pharmaceutical composition comprising an antibacterially effective amount of a compound having the formula

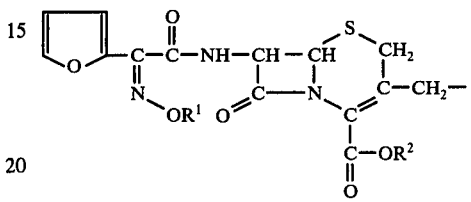

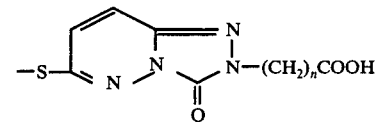

wherein $R^1$ is alkyl containing 1-4 carbon atoms, $n$ is 1 or 2 and $R^2$ is hydrogen, pivaloyloxymethyl, acetoxymethyl, methoxymethyl, acetonyl, phenacyl, p-nitrobenzyl, β,β,β-trichloroethyl, 3-phthalidyl or nitrobenzyl, β,β,β-trichloroethyl, 3-phthalidyl or 5-indanyl and preferably is hydrogen or a nontoxic, pharmaceutically 75% by weight in the form of its syn isomer and preferably in the form of its syn isomer essentially free of the corresponding anti isomer, and a pharmaceutically acceptable carrier therefor.

There is further provided by the present invention a pharmaceutical composition comprising an antibacterially effective amount of the syn isomer of a compound having the formula

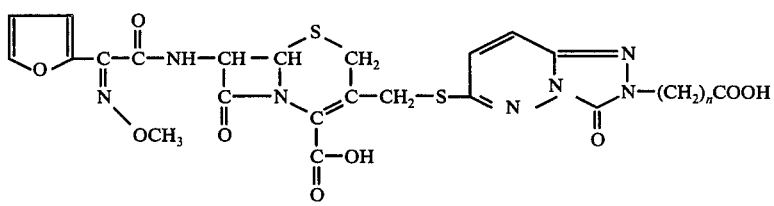

wherein $n$ is 1 or 2 or a nontoxic, pharmaceutically acceptable salt thereof and wherein $n$ is preferably 1, and a pharmaceutically acceptable carrier therefor.

There is further provided by the present invention a method of treating bacterial infections comprising administering by injection to an infected warm-blooded animal, including man, an effective but nontoxic dose of 250–1000 mgm. of a compound having the formula

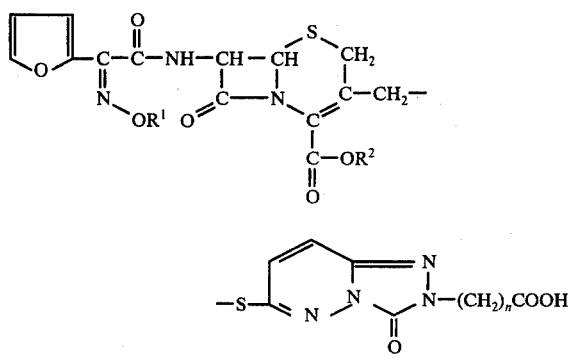

wherein $R^1$ is alkyl containing 1–4 carbon atoms, $n$ is 1 or 2 and $R^2$ is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl or a nontoxic, pharmaceutically acceptable salt thereof, said compound being a least 75% by weight in the form of its syn isomer and preferably in the form of its syn isomer essentially free of the corresponding anti isomer.

There is further provided by the present invention a method of treating bacterial infections comprising administering by injection to an infected warm-blooded animal, including man, an effective but nontoxic dose of 250–1000 mgm. of the syn isomer of a compound having the formula

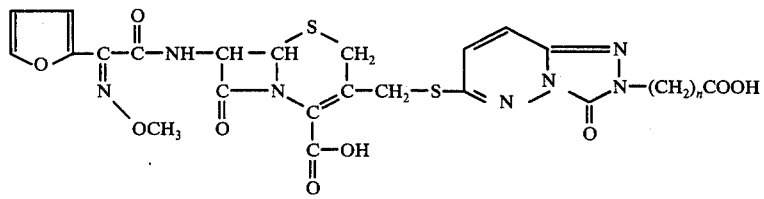

wherein $n$ is 1 or 2 or a nontoxic, pharmaceutically acceptable salt thereof and wherein $n$ is preferably 1.

There is also provided by the present invention a method for combatting Haemophilus infections which comprises administering to a warm-blooded mammal infected with an Haemophilus infection an amount effective for treating said Haemophilus infection of a composition comprising a compound having the formula

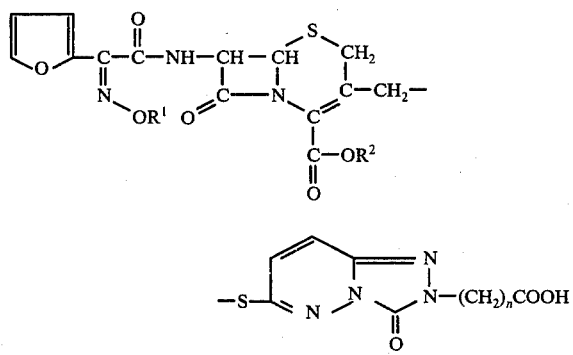

wherein $R^1$ is alkyl containing 1–4 carbon atoms, $n$ is 1 or 2 and $R^2$ is hydrogen, pivaloyloxymethyl, acetoxymethyl, methoxymethyl, acetonyl, phenacyl, p-nitrobenzyl, β,β,β-trichloroethyl, 3-phthalidyl or nitrobenzyl, β,β,β-trichloroethyl, 3-phthalidyl or 5-indanyl and preferably is hydrogen or a nontoxic, pharmaceutically acceptable salt thereof, said compound being at least 75% by weight in the form of its syn isomer and preferably in the form of its syn isomer essentially free of the corresponding anti isomer, and a pharmaceutically acceptable carrier therefor.

There is also provided by the present invention a method for combatting Neisseria infections which comprises administering to a warm-blooded mammal infected with a Neisseria infection an amount effective for treating said Neisseria infection of a composition comprising a compound having the formula

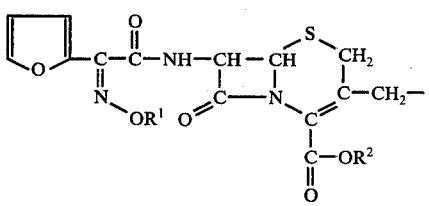

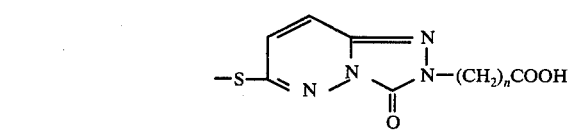

wherein $R^1$ is alkyl containing 1–4 carbon atoms, $n$ is 1 or 2 and $R^2$ is hydrogen, pivaloyloxymethyl, acetoxymethyl, methoxymethyl, acetonyl, phenacyl, p-nitrobenzyl, β,β,β-trichloroethyl, 3-phthalidyl or nitrobenzyl, β,β,β-trichloroethyl, 3-phthalidyl or 5-indanyl and preferably is hydrogen or a nontoxic, pharmaceutically acceptable salt thereof, said compound being at least 75% by weight in the form of its syn isomer and preferably in the form of its syn isomer essentially free of the corresponding anti isomer, and a pharmaceutically acceptable carrier therefor.

We claim:
1. A compound having the formula

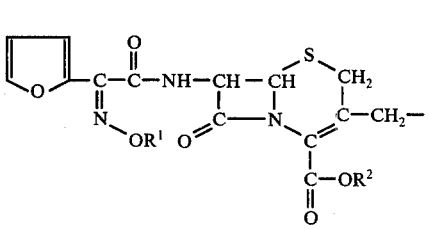

-continued

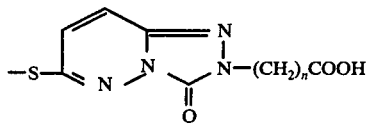

wherein $R^1$ is alkyl of 1–4 carbon atoms, $n$ is 1 or 2 and $R^2$ is hydrogen or pivaloyloxymethyl, acetoxymethyl, methoxymethyl, acetonyl, phenacyl, p-nitrobenzyl, β,β,β-trichloroethyl, 3phthalidyl or 5-indanyl or a nontoxic, pharmaceutically acceptable salt thereof, said compound being a least 75% by weight in the form of its syn isomer.

2. The syn isomer of a compound having the formula

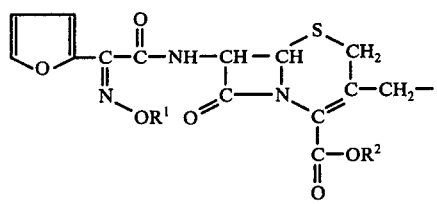

wherein $R^1$ is alkyl of 1–4 carbon atoms, $n$ is 1 or 2 and $R^2$ is hydrogen, pivaloyloxymethyl, acetoxymethyl, methoxymethyl, acetonyl, phenacyl, p-nitrobenzyl, β,β,β-trichloroethyl, 3-phthalidyl or 5-indanyl or a nontoxic, pharmaceutically acceptable salt thereof.

3. The syn isomer of a compound having the formula

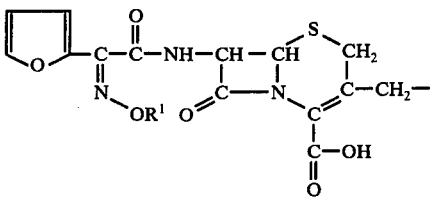

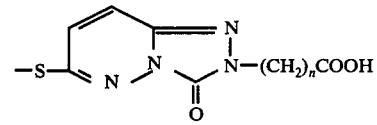

wherein $R^1$ is alkyl of 1–4 carbon atoms and $n$ is 1 or 2 or a nontoxic, pharmaceutically acceptable salt thereof.

4. The syn isomer of a compound having the formula

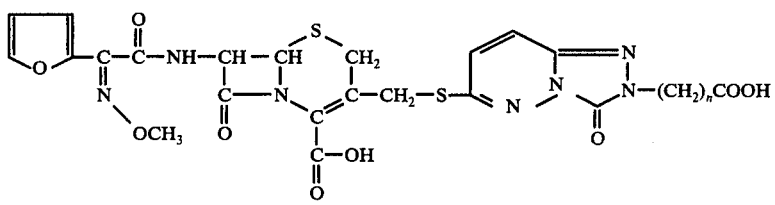

wherein $n$ is 1 or 2 or a nontoxic, pharmaceutically acceptable salt thereof.

5. A compound of claim 4 wherein $n$ is 1.
6. A compound of claim 4 wherein $n$ is 2.
7. The syn isomer of a compound having the formula

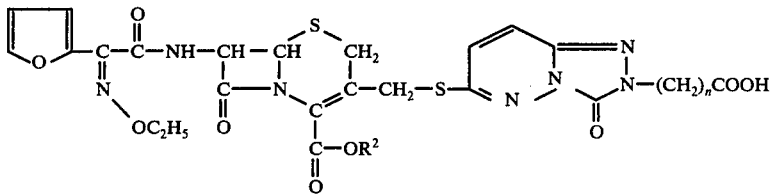

wherein $n$ is 1 or 2 or a nontoxic, pharmaceutically acceptable salt thereof.

8. A compound of claim 7 wherein $n$ is 1.
9. A compound of claim 7 wherein $n$ is 2.

* * * * *